United States Patent
Kim

(10) Patent No.: US 10,359,362 B2
(45) Date of Patent: Jul. 23, 2019

(54) METHOD FOR MANUFACTURING NANOPARTICLE ARRAY, SURFACE PLASMON RESONANCE-BASED SENSOR AND METHOD FOR ANALYZING USING SAME

(71) Applicant: Plexense, Inc., Davis, CA (US)

(72) Inventor: Gibum Kim, Sacramento, CA (US)

(73) Assignee: Plexense, Inc., Davis, CA (US)

( * ) Notice: Subject to any disclaimer, the term of this patent is extended or adjusted under 35 U.S.C. 154(b) by 681 days.

(21) Appl. No.: 14/784,569

(22) PCT Filed: Sep. 10, 2013

(86) PCT No.: PCT/KR2013/008182
§ 371 (c)(1),
(2) Date: Feb. 4, 2016

(87) PCT Pub. No.: WO2014/171597
PCT Pub. Date: Oct. 23, 2014

(65) Prior Publication Data
US 2016/0146733 A1    May 26, 2016

(30) Foreign Application Priority Data

Apr. 15, 2013  (KR) ........................ 10-2013-0041228
Jul. 15, 2013  (KR) ........................ 10-2013-0083142

(51) Int. Cl.
*G01N 33/00* (2006.01)
*G01N 21/552* (2014.01)
*B81C 1/00* (2006.01)

(52) U.S. Cl.
CPC ......... *G01N 21/554* (2013.01); *B81C 1/0038* (2013.01); *G01N 2201/068* (2013.01)

(58) Field of Classification Search
None
See application file for complete search history.

(56) References Cited

U.S. PATENT DOCUMENTS 6,429,023 B1   8/2002   Gharavi
6,645,343 B1   11/2003  Wild et al.
(Continued)

FOREIGN PATENT DOCUMENTS

EP   1601512 A1   12/2005
EP   1644517 A1   4/2006
(Continued)

OTHER PUBLICATIONS

C.-P. Klages, et al, "Microplasma-Based Treatment of Inner Surfaces in Microfluidic Devices", Contrib. Plasma Phys. 47, No. 1-2, pp. 49-56 (2007).
(Continued)

*Primary Examiner* — Robert T. Crow
(74) *Attorney, Agent, or Firm* — Knobbe, Martens, Olson & Bear, LLP

(57) ABSTRACT

The present invention relates to a method for manufacturing a nanoparticle array, a surface plasmon resonance-based sensor, and a method for analyzing using the same. According to one embodiment of the present invention, after a mixed solution of an ionized binder and conductive nanoparticles is prepared, a substrate is dipped into the mixed solution. Thereafter, by applying an electric field to the mixed solution into which the substrate is dipped so as to induce coating of the conductive nanoparticles on the substrate, it is possible to manufacture, by a wet method, a nanoparticle array in which the conductive nanoparticles are quickly coated on the substrate with high density.

22 Claims, 7 Drawing Sheets

(56) References Cited

U.S. PATENT DOCUMENTS

| | | | |
|---|---|---|---|
| 6,770,721 B1 | 8/2004 | Kim | |
| 6,818,259 B1 | 11/2004 | Koontz | |
| 7,327,000 B2 | 2/2008 | DeHeer et al. | |
| 7,652,760 B1 | 1/2010 | Simpson et al. | |
| 7,731,826 B2 | 6/2010 | Hibbs et al. | |
| 8,039,379 B1* | 10/2011 | Alers | H01L 21/76858 257/E21.174 |
| 10,060,851 B2 | 8/2018 | Kim | |
| 2002/0068170 A1* | 6/2002 | Smalley | B82Y 10/00 428/403 |
| 2002/0128234 A1 | 9/2002 | Hubbell et al. | |
| 2003/0082237 A1 | 5/2003 | Cha et al. | |
| 2004/0055892 A1* | 3/2004 | Oh | B82Y 10/00 205/109 |
| 2004/0154541 A1 | 8/2004 | Colpo et al. | |
| 2006/0099750 A1 | 5/2006 | DeHeer et al. | |
| 2006/0274314 A1 | 12/2006 | Thomsen et al. | |
| 2007/0154351 A1 | 7/2007 | Bae et al. | |
| 2007/0178280 A1 | 8/2007 | Bower et al. | |
| 2007/0285843 A1* | 12/2007 | Tran | B82Y 10/00 360/245.9 |
| 2008/0041733 A1 | 2/2008 | Hibbs et al. | |
| 2008/0044592 A1 | 2/2008 | Elkin et al. | |
| 2008/0131869 A1 | 6/2008 | Frederix et al. | |
| 2009/0117669 A1 | 5/2009 | Yamamichi et al. | |
| 2009/0142789 A1 | 6/2009 | Aastrup et al. | |
| 2009/0209420 A1 | 8/2009 | Kalgutkar et al. | |
| 2010/0068824 A1 | 3/2010 | Kimura | |
| 2010/0123900 A1 | 5/2010 | Chau et al. | |
| 2010/0134799 A1 | 6/2010 | Huh et al. | |
| 2010/0215555 A1 | 8/2010 | Jin et al. | |
| 2011/0207237 A1 | 8/2011 | Sai et al. | |
| 2011/0281070 A1 | 11/2011 | Mittal et al. | |
| 2011/0297212 A1 | 12/2011 | Wu et al. | |
| 2012/0241693 A1 | 9/2012 | Magdassi et al. | |
| 2012/0263793 A1* | 10/2012 | Vitaliano | G01N 21/554 424/490 |
| 2013/0029057 A1 | 1/2013 | Laksin et al. | |
| 2014/0132954 A1 | 5/2014 | Kang et al. | |
| 2016/0146733 A1 | 5/2016 | Kim | |
| 2016/0161406 A1 | 6/2016 | Kim | |

FOREIGN PATENT DOCUMENTS

| | | |
|---|---|---|
| EP | 2128598 A1 | 12/2009 |
| EP | 1676330 B1 | 5/2010 |
| EP | 2386070 A1 | 11/2011 |
| EP | 2391657 A1 | 12/2011 |
| EP | 2 700 455 A1 | 2/2014 |
| EP | 3 139 154 A1 | 3/2017 |
| JP | 62-102139 A | 5/1987 |
| JP | 62-187248 A | 8/1987 |
| JP | 7-47265 A | 2/1995 |
| JP | 10-307104 A | 11/1998 |
| JP | 2002-357540 A | 12/2002 |
| JP | 2005-037403 | 2/2005 |
| JP | 2005-121499 | 5/2005 |
| JP | 2005-181296 | 7/2005 |
| JP | 3730652 B2 | 10/2005 |
| JP | 3897703 B2 | 1/2007 |
| JP | 2007-093590 | 4/2007 |
| JP | 2008-175615 A | 7/2008 |
| JP | 2008-216055 A | 9/2008 |
| JP | 2008-232853 A | 10/2008 |
| JP | 4220879 B2 | 11/2008 |
| JP | 2009-57263 | 3/2009 |
| JP | 4481967 B2 | 3/2010 |
| JP | 2010-155218 | 7/2010 |
| JP | 2012-098211 A | 5/2012 |
| JP | 2012-132886 A | 7/2012 |
| KR | 10-0136144 B1 | 1/1998 |
| KR | 10-1996-0023241 | 7/1998 |
| KR | 10-1999-0008697 | 2/1999 |
| KR | 10-0265692 B1 | 9/2000 |
| KR | 10-2002-0075387 A | 10/2002 |
| KR | 10-2003-0079325 | 10/2003 |
| KR | 10-0465278 B1 | 1/2005 |
| KR | 10-0480340 B1 | 3/2005 |
| KR | 10-2006-0094409 A | 8/2006 |
| KR | 10-0662021 B1 | 12/2006 |
| KR | 10-2007-0080914 | 8/2007 |
| KR | 10-2007-0100325 A | 10/2007 |
| KR | 10-0787046 B1 | 12/2007 |
| KR | 10-0860958 B1 | 9/2008 |
| KR | 10-2009-0054096 | 5/2009 |
| KR | 10-2009-0055191 | 6/2009 |
| KR | 10-2009-0060635 A | 6/2009 |
| KR | 10-2009-0087594 | 8/2009 |
| KR | 10-2009-0110228 | 10/2009 |
| KR | 10-0928546 B1 | 11/2009 |
| KR | 10-2009-0128276 | 12/2009 |
| KR | 10-2010-0007723 | 1/2010 |
| KR | 10-2010-0014314 A | 2/2010 |
| KR | 10-2010-0023335 | 3/2010 |
| KR | 10-2010-0061603 A | 6/2010 |
| KR | 10-2010-0063316 A | 6/2010 |
| KR | 10-2010-0069087 | 6/2010 |
| KR | 10-0962290 B1 | 6/2010 |
| KR | 10-2010-0106263 A | 10/2010 |
| KR | 10-2010-0112781 | 10/2010 |
| KR | 10-0987993 B1 | 10/2010 |
| KR | 10-0991011 B1 | 10/2010 |
| KR | 10-2010-0119630 | 11/2010 |
| KR | 10-0996450 B1 | 11/2010 |
| KR | 10-2011-0033575 | 3/2011 |
| KR | 10-1017994 B1 | 3/2011 |
| KR | 10-1027795 B1 | 4/2011 |
| KR | 10-1029115 B1 | 4/2011 |
| KR | 10-2011-0056118 | 5/2011 |
| KR | 10-2011-0071984 | 6/2011 |
| KR | 10-2011-0079139 | 7/2011 |
| KR | 10-2011-0124489 A | 11/2011 |
| KR | 10-2011-0128122 | 11/2011 |
| KR | 10-1079271 B1 | 11/2011 |
| KR | 10-1081336 B1 | 11/2011 |
| KR | 10-2011-0139376 | 12/2011 |
| KR | 10-1097882 B1 | 12/2011 |
| KR | 10-2012-0013770 A | 2/2012 |
| KR | 10-2012-0014206 A | 2/2012 |
| KR | 10-2012-0016598 A | 2/2012 |
| KR | 10-1124618 B1 | 3/2012 |
| KR | 10-1134349 B1 | 4/2012 |
| KR | 10-1145133 B1 | 5/2012 |
| KR | 10-1145660 B1 | 5/2012 |
| KR | 10-2012-0060968 | 6/2012 |
| KR | 10-2012-0084529 A | 7/2012 |
| KR | 10-1175977 B1 | 8/2012 |
| KR | 10-2012-0099957 | 9/2012 |
| KR | 10-2012-0136912 A | 12/2012 |
| KR | 10-2013-0000583 A | 1/2013 |
| KR | 10-2013-0006169 A | 1/2013 |
| KR | 10-2013-0015806 A | 2/2013 |
| KR | 10-1238551 B1 | 3/2013 |
| KR | 10-1239356 B1 | 3/2013 |
| KR | 10-2013-0041228 | 4/2013 |
| KR | 10-1254666 B1 | 4/2013 |
| KR | 10-1271418 B1 | 6/2013 |
| KR | 10-2013-0083142 | 7/2013 |
| KR | 10-1328190 B1 | 11/2013 |
| KR | 10-2012-0136912 | 12/2013 |
| KR | 10-1335032 B1 | 12/2013 |
| KR | 10-2014-0124316 A | 10/2014 |
| WO | 2004-080681 A1 | 9/2004 |
| WO | 2005-001120 A1 | 6/2005 |
| WO | WO 2007/127989 A2 | 11/2007 |
| WO | 2010-078666 A1 | 7/2010 |
| WO | 2010-085945 A1 | 8/2010 |
| WO | 2012-111991 A9 | 8/2012 |
| WO | 2012-157403 A1 | 11/2012 |
| WO | 2014-137152 A1 | 9/2014 |

(56) References Cited

FOREIGN PATENT DOCUMENTS

| WO | 2014-171597 A1 | 10/2014 |
|---|---|---|
| WO | WO 2016/099954 A1 | 6/2016 |

OTHER PUBLICATIONS

Osamu Takai, "Solution plasma processing (SPP)", Pure Appl. Chem., vol. 80, No. 9, pp. 2003-2011, 2008—9 pages.
Sung Min Kim, et al., "Effects of PVP and KCl concentrations on the synthesis of gold nanoparticles using a solution plasma processing", Department of Material Engineering, Korea Aerospace University and Research Institute for Aerospace Engineering—3 pages.
Khoren Sahagian, et al, "Why and How to Use Gas Plasma Technology for Surface Treatment in Medical Devices", Published on MDDI Medical Device and Diagnostic Industry News Products and Suppliers (http://www.mddionline.com)—7 pages.
Christiane Gottschalk et al., "Using dissolved ozone in semiconductor cleaning applications", Micro, A Canon Communications LLC Publication, Mar. 2004—6 pages.
Anjum Qureshi, et al, "Surface Modification of Polycarbonate by Plasma Treatment", iopscience.iop.org, Journal of Physics: Conference Series 208 (2010) 012108—7 pages.
Peter Bruggeman, et al., "Non-thermal plasmas in and in contact with liquids", J. Phys. D: Appl. Phys. 42 (2009) 053001—29 pages.
Helena Oi Lun Li, et al., "Comparison between the Mechanism of Liquid Plasma Discharge Process in Water and Organic Solution", Green Mobility Collaborative Research Center, Nagoya University, Graduate School of Engineering, Nagoya University, dated Dec. 14, 2012, pp. 22-27.
K. Baba, et al., "Ion irradiation effects on ionic liquids interfaced with rf discharge plasmas", Department of Electronic Engineering, Tohoku University, Sendai 980-8579, Japan, Appl. Phys. Lett. 90, 201501 2007—4 pages.
Rajesh Dorai, et al., "Plasma Surface Modification of Polymers Using Atmospheric Pressure Discharges", University of Illinois Department of Chemical Engineering and Department of Electrical and Computer Engineering—32 pages.
Dorota Kregiel, et al., "Effect of Plasma Processing and Organosilane Modifications of Polyethylene on Aeromonas hydrophila Biofilm Formation", Hindawi Publishing Corporation BioMed Research International vol. 2014, Article ID 232514—9 pages.
Ron Nickerson, "Plasma Surface Modification for Cleaning and Adhesion", AST Products, Inc.—6 pages.
Nina Recek, et al., "Protein Adsorption on Various Plasma-Treated Polyethylene Terephthalate Substrates", Molecules 2013, 18, 12441-12463; doi:10.3390/molecules181012441—23 pages.
Qiang Chen, et al., "Plasma-Liquid Interaction: a New Way to Synthesize Nanomaterials", Fujian Provincial Key Laboratory of Plasma and Magnetic Resonance, School of Physics and Mechanical and Electrical Engineering, Department of Physics, Lanzhou University and State Key Laboratory of Heavy Oil Processing, China University of Petroleum—73 pages.
Plasma Surface Modification of Polymers, 2007 PLASMATech—2 pages.
Toshiro Kaneko, et al., "Plasma Process on Ionic Liquid Substrate for Morphology Controlled Nanoparticles", http://dx.doi.org/10.5772/52095—16 pages.
Dr. James D. Getty, March Plasma Systems, "How Plasma-Enhanced Surface Modification Improves the Production of Microelectronics and Optoelectronics", Chip Scale Review 2002—pp. 72-75.
Frank Endres, et al., "Electrodeposition from Ionic Liquids", Yokohama, Japan, Dec. 2007—399 pages.
Yudai Minagawa, et al., "Analysis of effect of ion irradiation to liquid surface on water molecule kinetics by classical molecular dynamics simulation", iopscience.iop.org—8 pages.
Kenichi Uemura, et al., "Cleaning Technology of Silicon Wafers", Nippon Steel Technical Report No. 83 Jan. 2001—8 pages.
V. Colombo, et al., "Atmospheric Plasma Surface Modification of Electrospun Poly(L-Lactic Acid): Effect on MAT Properties and Cell Culturing", 22nd Annual BioInterface Conference, Oct. 2012—32 pages.
International Search Report dated Jun. 3, 2014 of related PCT Application No. PCT/KR2014/001799 and its English translation—4 pages.
International Search Report dated Jan. 9, 2014 of PCT Application No. PCT/KR2013/008182 which is the parent application and its English translation—4 pages.
Invitation to Pay Additional Fees issued by the International Searching Authority in International Application No. PCT/US15/63954 dated Feb. 10, 2016.
International Search Report and Written Opinion issued for International application No. PCT/US15/63954 dated Apr. 8, 2016.
U.S. Appl. No. 16/053,631, filed Aug. 2, 2018, Kim.
Takai, "Solution plasma processing (SPP)", Pure Appl. Chem., vol. 80, No. 9, pp. 2003-2011, 2008.
Extended European Search Report for application No. 15870682.0-1103; dated Jul. 24, 2018; 3 pages.
Notice of Allowance dated Oct. 22, 2018 in Japanese Application No. 2017-550465.
Supplementary Search Report dated Jul. 17, 2018 in European Patent Application No. 15870682; 2 pages.
Office Action dated Jun. 25, 2018 in Japanese Patent Application No. 2017-550465; 15 pages.
Office Action dated Nov. 5, 2018 in U.S. Appl. No. 14/773,304; 34 pages.

* cited by examiner

METHOD FOR MANUFACTURING NANOPARTICLE ARRAY, SURFACE PLASMON RESONANCE-BASED SENSOR AND METHOD FOR ANALYZING USING SAME

TECHNOLOGICAL FIELD

The present invention describes a sensor technology for detecting biological or non-biological substances. In more detail, a method for manufacturing a nanoparticle array, a surface plasmon resonance-based sensor and a method for analyzing using the same.

BACKGROUND TECHNOLOGY

A surface plasmon resonance (SPR) refers to a phenomenon of the propagation of surface plasmon polaritons (SPPs) which are formed on or near the surface of conductive materials by coupling of electrons and photons having a specific wavelength. In general, SPR is a collective oscillation of conduction band electrons propagating along the interface between a metal with a negative dielectric constant and a medium with a positive dielectric constant. SPR has an enhanced intensity in comparison with an incident electromagnetic wave and shows characteristics of an evanescent wave which exponentially decreases as getting far-off perpendicularly from the interface.

The SPR can be classified as propagating plasmons observed at the interface between a 10~200 nm-thick flat metal surface and a dielectric substance; and a localized SPR (LSPR) observed from nanoparticles or nanostructures. LSPR detects a change in the SPR wavelength showing maximum absorbance or scattering which depends on a change of the chemical and physical environment on the surface (for example, a change in refractive index of a medium near the surface) of nanoparticles or nanostructures. A LSPR-based sensor has many merits over a conventional bulk SPR sensor which utilizes a plasmon propagation by prism coupling, because the detection of the SPR wavelength change permits to distinguish specific molecules or to analyze concentration of specific molecules in a medium; LSPR is highly sensitive to the change of refractive index and that allows label-free detection.

Nano-patterning technologies, such as an electron beam lithography, a focused ion beam, and a nano-imprint, have been proposed as methods for preparing metal nanoparticle array to induce LSPR. However, such conventional technologies have limitations in improving production yield upon applying continuous processes or various substrate sizes. Furthermore, the conventional technologies often lead to defective products due to defects or contaminations, in the case of requiring a mechanical contact. As another manufacturing method, a technology was proposed to deposit a metal thin film having a continuous profile and then thermally anneal to form an array of nano-islands isolated each other. In this case, however, substrate materials for nano-island formation are limited to heat-resisting materials such as glass and there is a problem of not obtaining a nanoparticle array with a high nanoparticle density.

DETAILED DESCRIPTION OF THE INVENTION

Technical Problems

The technical problems which the present invention aims to solve is to provide a method for manufacturing a nanoparticle array which allows a high production yield upon applying continuous production processes; a wide window for selecting a substrate material due to capability of a low or room temperature production process; and immobilization of high density conductive nanoparticles on a substrate to enhance SPR or LSPR amplification effect.

In another aspect, another technical problem which the present invention aims to solve is to offer a SPR- or LSPR-based sensor which is manufactured using the stated nanoparticle array and has an enhanced spectroscopic analysis sensitivity.

In another aspect, another technical problem which the present invention aims to solve is, using the stated sensor, to offer a spectroscopic analysis method having a simple analysis process, quick response and high reliability.

Solutions for Technical Problems

In the first embodiment to solve the stated technical problem, a method for manufacturing a nanoparticle array comprises a process providing a mixed solution of an ionic binder and conductive nanoparticles; a process dipping a substrate into the mixed solution; a process applying an electric field to the substrate-dipped mixed solution for inducing coating of conductive nanoparticles onto the substrate.

In the second embodiment to solve the stated different technical problem, a spectroscopic analysis sensor comprises a substrate; a polymer binder layer coated on the substrate; conductive nanoparticles dispersed and immobilized on the polymer binder layer. The sensor can be a SPR-based spectroscopic analysis sensor.

In the third embodiment to solve the stated another different technical problem, a spectroscopic analysis method comprises a process dipping a spectroscopic analysis sensor into a target analyte-dispersed solution; a process detecting change of reflected or transmitted light on a surface of the sensor using SPR or LSPR. In another different embodiment, the above stated spectroscopic analysis method includes a process dipping two or more sensors spacially isolated and stacked into a target analyte-dispersed solution; a process detecting change in SPR- or LSPR mode-coupled reflected or transmitted light upon applying an incident light onto the sensor.

Effect of the Invention

Referring to the present invention, a cost-effective wet method to manufacture a nanoparticle array can be offered through quick and high density coating of metal nanoparticles onto the substrate by dipping the substrate into a mixed solution of an ionic binder and conductive nanoparticles followed by applying an electric filed outside.

In addition, referring to the present invention, a sensor with an enhanced detection sensitivity, which depends on a kind and concentration of a target analyte, can be offered by adapting the high metal nanoparticle density sensor for a SPR or LSPR mode-based spectroscopic analysis. In addition, in the case of performing a SPR or LSPR-based spectroscopic analysis after multiple stacking of the stated sensor, it can be easy to amplify a measurement sensitivity practically as much as the number of stacked sensor through the effect of an increased conductive metal nanoparticle density per unit light transmitted area.

PREFERRED EMBODIMENTS OF THE INVENTION

Figure 1:
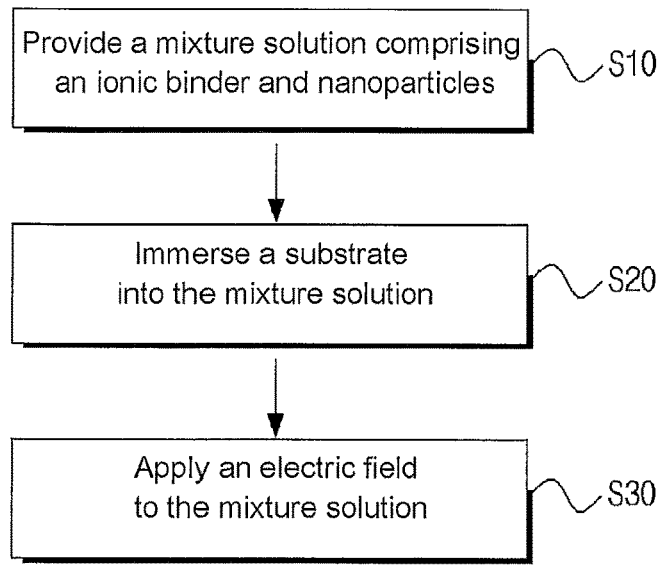
FIG. 1 is a flow chart for explaining a nanoparticle array manufacturing method, referring to the first embodiment in the present invention.

Preferred embodiments of the present invention are described in detail referring to the accompanied drawings.

The embodiments in the present invention aim to provide more complete explanation of the invention to people who have common knowledge in the stated technological fields. The following embodiments can be modified to various different forms and the scope of the present invention is not limited to the following embodiments. Rather, those embodiments make all the invention more faithful and complete and aim to completely deliver the idea of the present invention to people skilled in the relevant technology.

In drawings, a same mark indicates a same element. In addition, as used in the specification of the present invention, the terminology "and/or" includes one and all combinations of more than one among the items listed.

The terminologies used in the present specification are used for explaining the embodiments and are not intended to limit the scope of the present invention. In addition, even though a word in the specification has a singular form, it can include a plural form if not clearly indicating a singular form in the context. In addition, the terminologies "comprise" and "comprising" used in the specification specify the mentioned shapes, numbers, stages, actions, absence, elements and/or the presence of these group. They do not exclude different shapes, numbers, stages, actions, absence, elements and/or the presence or addition of the group.

In the specification, mentioning a substrate or a layer formed on a different layer can refer to a layer formed directly above the mentioned substrate or the different layer, a mid-layer formed on the mentioned substrate or the different layer, or a layer formed between the mid-layers. In addition, for people skilled in relevant technological fields, the structure and shape placed adjacent to a different shape can be overlapped with the adjacent shape or have a portion placed below.

In the present specification, words indicating a relative direction such as "below", "above", "upper", "lower", "horizontal" and "vertical", as illustrated in the drawings, can be used for describing a part of compartment, a compartment of a different layer or region, a relationship of a layer or region. It should be understood that these words encompass different directions of the component as well as the directions shown in the drawings.

Following this, the embodiments of the present invention will be explained referring to cross sectional drawings schematically illustrating ideal embodiments (and mid-structures) of the present invention. In the drawings, for example, the size and shape of the compartments can be exaggerated for convenience and clarity in explanation and it can be expected to modify the shape illustrated upon a real embodiment. Thus, the embodiments of the present invention should not be interpreted such that they are limited only to the specific shapes illustrated in the specification. In addition, reference marks for the compartments on drawings indicate the same compartments in the entire drawings.

FIG. 1 is a flow chart for explaining a nanoparticle array manufacturing method referring to the first embodiment of the present invention and FIGS. 2a-2e illustrate a nanoparticle array manufacturing method referring to the first embodiment of the present invention.

Figure 2A:
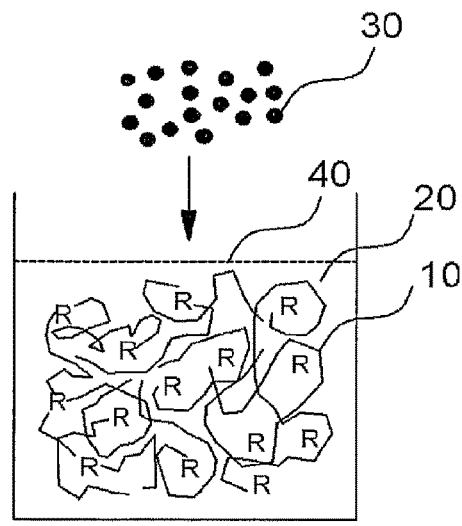
FIGS. 2a-2e illustrate a method for manufacturing a nanoparticle array, referring to the first embodiment in the present invention.

Referring to FIGS. 1 and 2a, it is possible to prepare a mixed solution (40) by dissolving an ionic binder (10) in an appropriate solvent followed by dispersing conductive metal nanoparticles (30) in the above stated solution; or by adding an ionic binder (10) into the solvent (20) dispersed with conductive nanoparticles (30) (S10). In the mixed solution (40), an ionic binder (10) and conductive metal nanoparticles (30) bind together and can form a gel. In some embodiments, the mixed solution (40) can be stirred for achieving homogeneous dispersion of the conductive nanoparticles and preventing their coagulation; or applied to ultrasonic energy for preventing coagulation of the conductive nanoparticles.

An ionic binder (10) can be a polymer bearing a cationic or anionic charge in the mixed solution (40). In the first embodiment, the polymer can be selected among ionic polymers having a molecular weight between 1,000 kDa and 60,000 kDa. In the case of the polymer having a molecular weight less than 1,000 kDa, an immobilization force between the conductive nanoparticles and the substrate is not enough; whereas in the case of the polymer having a molecular weight larger than 60,000 kDa, it cannot be expected, due to very high viscosity, as will be discussed later, to have an enough flux even upon applying an electric field.

In the first embodiment, a cationic polymer can contain one or a mixture of poly diallydimethylammonium chloride, poly allylamine hydrochloride, poly 4-vinylbenzyltrimethyl ammonium chloride and polyethyleneimine an anionic polymer can contain one or a mixture of poly acrylic acid, poly sodium 4-styrene sulfonate, poly vinylsulfonic acid, poly sodium salt and poly amino acids. However, the above stated polymers are just some of many examples and thus the scope of polymers in the present invention includes polymers or copolymers having different ionic functional groups, polymers having cationic or anionic functional groups on the skeletal structures of the above stated polymers, different synthetic polymers, natural polymers, or electrolyte polymers.

The above stated solvent can be one or a mixture of water such as distilled water and deionized water, aliphatic alcohols, aliphatic ketones, eaters of aliphatic carboxylic acids, imides of aliphatic carboxylic acids, aromatic hydrocarbons, aliphatic hydrocarbons, acetonitrile and aliphatic sulfoxides. However, the above stated solvents are just some of many examples and thus the scope of the solvent in the present invention can include other polar solvents.

The conductive nanoparticles (20) binding with the above stated polymers (10) in the mixed solution (40) can have an average diameter between 10 nm and 200 mm; and have one or a combined shape of a sphere, nano tube, nano column, nano rod, nano pore and nano wire. The stated nanoparticles can have one of completely filled, porous and hollowed forms. The above stated conductive nanoparticles can be conductive particles of carbon, graphite, metalloids, metals, alloys of the above stated metalloids or metals, conductive metal oxides, and metal nitrides or core-shell type particles of a glass or dielectric polymer bead coated with a conductive layer such as a metal thin film.

The above stated metalloids can be one or an alloy of antimony (Sb), germanium (Ge) and arsenic (As). The above state metals are metals, transition metals or post transition metals and they can be one or an alloy of titanium (Ti), zinc (Zn), aluminum (Al), scandium (Sc), chromium (Cr), manganese (Mn), iron (Fe), cobalt (Co), nickel (Ni), copper (Cu), indium (In), tin (Sn), yttrium (Y), zirconium (Zr), niobium (Nb), molybdenum (Mo), ruthenium (Ru), rhodium (Rh), palladium (Pd), gold (Au), silver (Ag), platinum (Pt), strontium (Sr), tungsten (W), cadmium (Cd) and tantalum (Ta).

The above stated conductive metal oxides comprise, but not limited to, indium tin oxide (ITO), indium zinc oxide (IZO), aluminum-doped zinc oxide (AZO), gallium indium zinc oxide (GIZO) and zinc oxide (ZnO). In addition, the above stated conductive nitrides comprise, but not limited to, tungsten nitrides (WN).

The mixed solution (40) can contain 0.01 wt. %-0.3 wt. % of an ionic binder (20), 0.1 wt. %-0.3 wt. % of conductive nanoparticles (30) and a solvent. The above stated wt. % can be determined depending on the kinds of the ionic binder (20) and the conductive nanoparticles (30) and the present invention is not limited to the above stated wt. %. In some embodiments, there can be added dispersion stabilizers such as an alginic acid, alginic acid derivatives and their mixture or pH regulating agents such as boric acid, orthophosphoric acid, acetic acid, ascorbic acid and citric acid. Or, in the case of photo-sensitive ionic binders, photo-initiators can be added for bridging reaction.

Figure 2B:
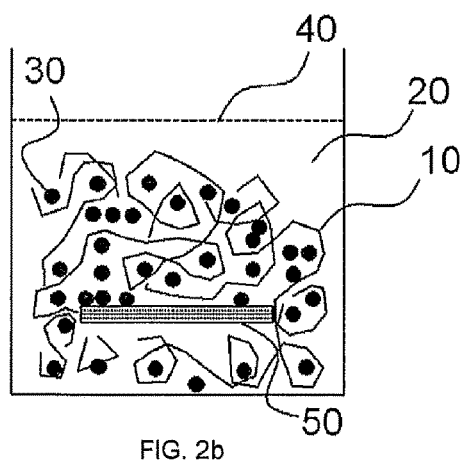

Referring to FIGS. 1a and 2b, the substrate (50) is immersed into the mixture solution (40). The substrate (50) can be fixed in a vessel by using an appropriate item and more than two substrates can be immersed. The substrate (50) can be washed or surface-treated before immersion.

The substrate (50) can be a transparent or opaque substrate, but transparent one is preferable. The thickness of the substrate can be within a range of 50 μm and 2 mm. The above stated transparent substrate, for example, can be a glass or polymeric material having 85% or higher optical transmittance. For example, the above stated polymeric materials can contain polycarbonate (PC), polyethylene terephthalate (PET), poly(methyl methacylate) (PMMA), triacetyl cellulose (TAC), cyclic olefin, polyarylate, polyacrylate, polyethylene naphthelate, polybutylene terephthalate or polyimide, but the scope of the present invention is not limited to the examples.

The above stated opaque substrate can include, but not limited to, sapphire or silicon single crystal. In addition, in other embodiments, a substrate (50) can include silicone rubbers, latexes or magnetic materials.

Figure 2C:
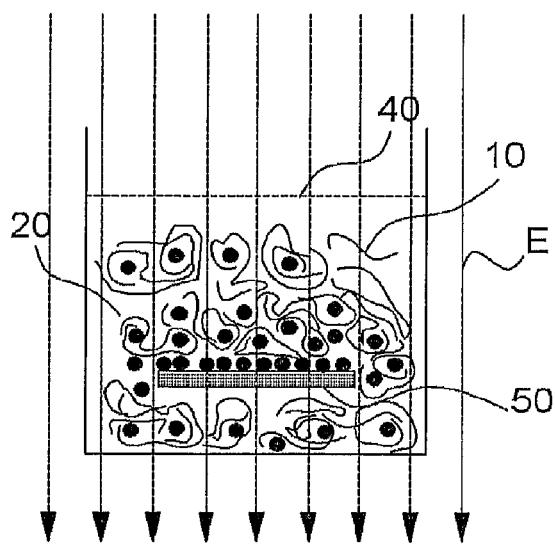

Referring to FIGS. 1a and 2c, an electric field (E) is applied to the mixed solution in which a substrate (50) is dipped. In some embodiments, the direction of an electric field can be determined according to the main surface, the surface where conductive nanoparticles will be mainly coated, of the substrate (50). For example, if want coating the conductive nanoparticles on the upper part of the substrate, an electric field can be formed downward direction perpendicular to the substrate when a cationic binder is used. Conversely, an electric field can be formed upward direction perpendicular to the substrate when an anionic binder is used.

The conductive nanoparticles (30) bound to an ionic binder can be accelerated toward the substrate by an electric field (E) inducing their electrophoretic movement which creates a directional flux of the conductive nanoparticles (30) toward the substrate (50). The above stated flux can be accelerated by an electric field and activated due to higher kinetic energy. That enhances coating speed of the conductive nanoparticles (30) onto the main surface of the substrate (50); increases immobilization power of the conductive nanoparticles (30); and allows high density coating of the conductive nanoparticles (30) on the substrate (50).

According to the embodiment of the present invention, the substrate (50) is in an electrically floating state because of its insulating nature; and an electric field (E) is generated outside the mixed solution (40) and penetrates inside the mixed solution (40). An electric field (E) can have, but not limited to, an electrostatic field, an alternating electric field or another type of waves. The above stated electric field (E) can be generated by plasma discharge in a chamber and details about this will be described later by referring to FIG. 3.

After that, the substrate (50) is retrieved from the mixed solution (40) upon sufficient immobilization of the conductive nanoparticles (30) onto the substrate (30). Then, the retrieved substrate (50) can be applied to a drying process; or ultraviolet light or heat to induce a bridging reaction of the binder. In some embodiments, a washing process of the substrate (50) can be performed. Unimmobilized conductive nanoparticles can be removed by the washing process followed by the contraction of the binder that occurs by a drying process.

Figure 2D:
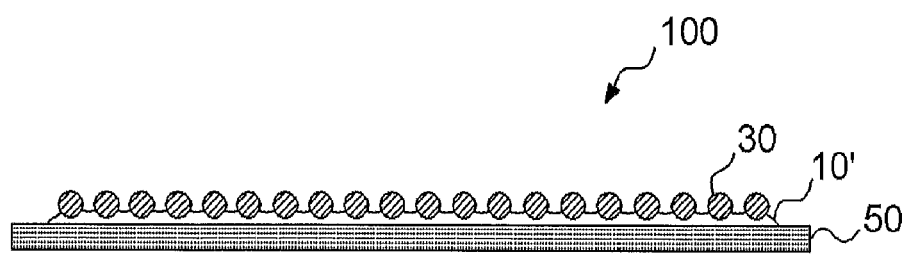

Referring to FIG. 2d, conductive nanoparticles (30) are immobilized on the substrate (50) by the polymeric binder layer (10') originated from a cationic binder. The conductive nanoparticles can form a monolayer of a nanoparticle array. In some embodiments, the upper surface of the conductive nanoparticles (30) is exposed upon the contraction of a polymeric binder layer (10') and thus, as will be described later, they can be used as a SPR- or LSPR-based sensor. In some embodiments, the stated polymeric binder layer (10') can be a dielectric substance.

Figure 2E:
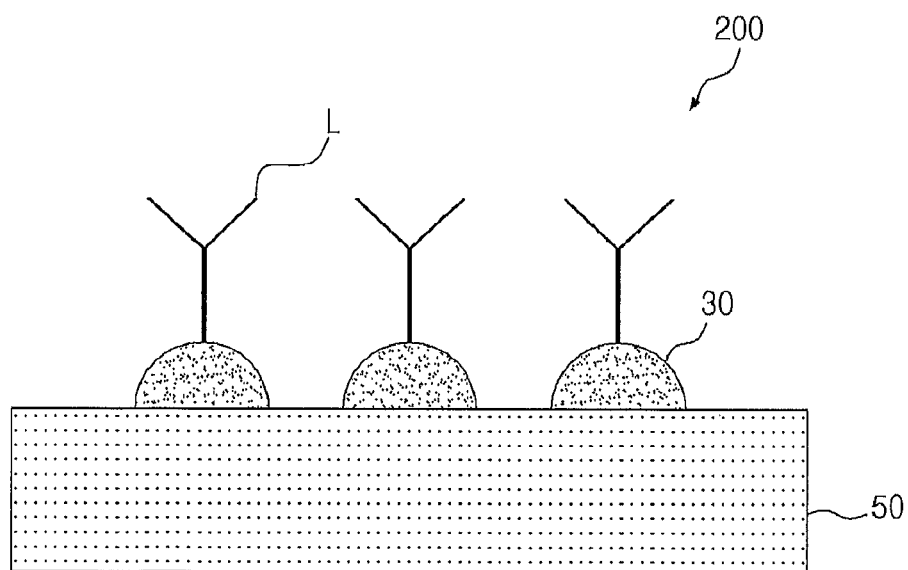

Referring to FIG. 2e, in some embodiments, it is possible to form an additional immobilization substance (L), on the conductive nanoparticles (30), which can specifically bind to target analytes. The immobilization substances (L) can be formed on the surface of the binder layer between conductive nanoparticles (30) besides the surface of the conductive nanoparticles (30). The immobilization substances (L) can be any one of low molecular weight compounds, antigens, antibodies, proteins, peptides, DNA, RNA, PNA, enzymes, enzyme substrates, hormones, and hormone receptors as well as any one of synthetic chemicals having functional groups, their mimics, or their combinations, which can bind to the target analytes. The method for their immobilization can be referred to the technology in the present article.

Figure 3:
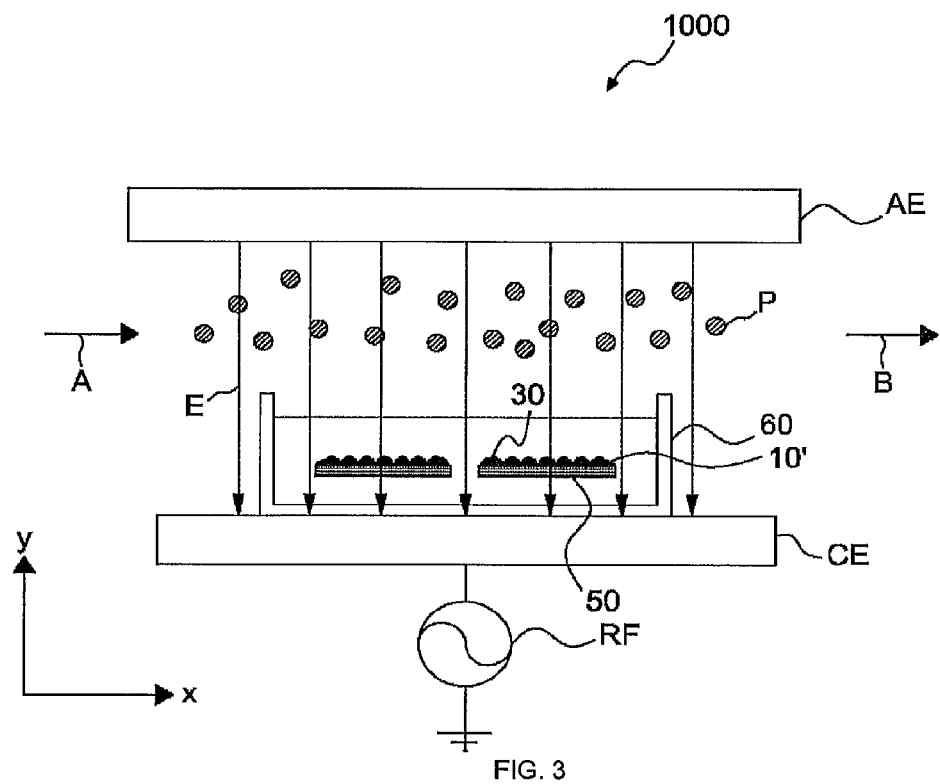
FIG. 3 illustrates an equipment for manufacturing a nanoparticle array, referring to the first embodiment in the present invention.

FIG. 3 illustrates an equipment (1000) for manufacturing a nanoparticle array according to the first embodiments of the present invention.

Referring to FIG. 3, the manufacturing equipment (1000) is an electric field (E) generator which is drawn referring to FIG. 2c. The manufacturing equipment (1000) can have two electrodes, an anode (AE) and a cathode (CE), to generate an electric field. In addition, the manufacturing equipment (1000) can have an adequate gas flow regulator for gas discharge.

A gas (P) is introduced into the space between the anode (AE) and the cathode (CE) as indicated using the arrow A and released continuously as indicated using the arrow B. In another embodiment, the gas (P) can be supplied from any one or both of the anode (A) and the cathode (B); and for gas supply the anode (AE) and the cathode (CE) can have penetration holes similar to those of a shower head.

The above stated gas can be one or a mixture of helium (He), neon (Ne), argon (Ar), nitrogen (N2) and air. However, these gases are some of many examples and thus the gas (P) can be other reactive gases.

A cathode (CE) can be electrically combined with an AC generator (a RF generator) for gaseous discharge of the gas (P), that is a generation of plasma, and an anode (AE) can be electrically grounded. Or, for DC discharge unlike the above stated AC discharge, a positive potential can be applied to the anode (AE) and a negative potential can be applied to the cathode (CE). After placing the container, containing the mixed solution (30) dipped with the substrate (50), between the cathode (CE) and the anode (AE), a process for immobilizing nanoparticles is performed for a few seconds to a few minutes while an electric power is supplied between the anode (AE) and/or the cathode for plasma generation. The distance between the anode (AE) and the container (6) can be maintained between 0.5 cm and 40 cm.

In the manufacturing equipment (1000) in FIG. 3, when applying an electric power to the AC generator of the cathode (CE), the cathode (CE) has negative potential due to self-bias and thus an electric field (E) is generated to the arrow direction between the anode (AE) and the cathode (CE) which are electrically grounded. The electric field generates a flux of the conductive nanoparticles and ionic binder in the mixed solution and by applying the electric field continuously for a few seconds to a few minutes the conductive nanoparticles can be immobilized on the substrate (50).

The location of the anode (AE) and cathode (CE) illustrated can be opposite. In addition, the anode (AE) is not limited to a flat shape and can have a side wall like a cap limiting a space for gaseous discharge or can be a main body of the chamber. In some embodiments, the pressure of the space for gaseous discharge can be an atmospheric pressure or a lower vacuum state for which a vacuum pump can be provided to the manufacturing equipment (1000).

Manufacturing a Nano Array

The mixed solution was prepared by adding 0.01 wt. % of an electrolyte polymer and 0.01 wt. % of a stabilizer as the previously stated ionic binder and 0.05 wt. % of gold nanoparticles as conductive nanoparticles into deionized water under magnetic stirring. Polyethylene terephthalate (PET) or polycarbonate (PC) was washed with deionized water, surface-treated and then dipped into the mixed solution. After that, a nano array was manufactured by proceeding a coating reaction in which the above stated mixed solution was placed inside the electric field generator and then an electric field was penetrated through the mixed solution for quick and homogeneous coating of the conductive nanoparticles bound to the ionic binder onto the above stated substrate.

As previously stated, to compare coating time, in the same mixed solution, in the cases of applying an electric field (referred to as an embodiment) and no electric field (referred to as a comparative example), absorbance measurement was performed after conductive nanoparticle coating. In the case of the embodiment, within 5 minutes, an absorbance value reached to 0.5 and thus a coating process for achieving an appropriate coating density was completed. However, in the case of the comparative example, it took at least 12 hours to obtain a coating density corresponding to the absorbance value of 0.2.

Figure 4A:
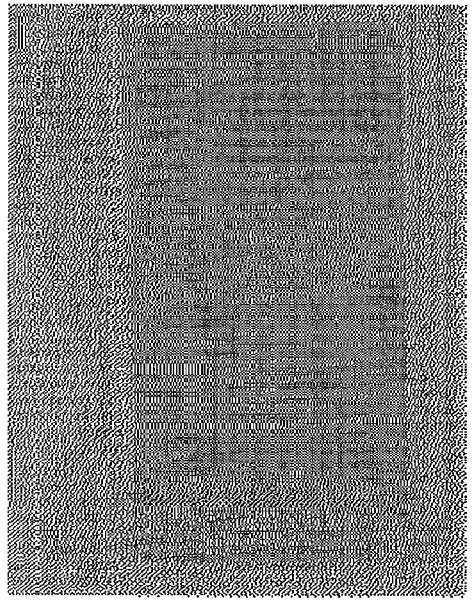
FIGS. 4a and 4b are optical images of gold nanoparticle arrays manufactured referring to the above embodiment and the above comparative example, respectively, in the present invention.
Figure 4B:
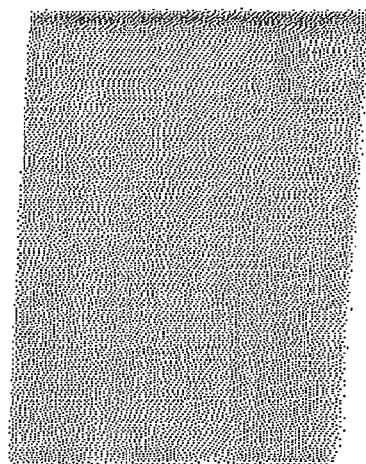

FIGS. 4a and 4b are optical picture images of the gold nanoparticle arrays manufactured referring to the embodiment and comparative example, respectively. The substrate used is polyethylene terephthalate (PET). Referring to FIGS. 4a and 4b, it is clearly seen that the case following the embodiment shows darker color than the case following the comparative example. This observation indicates that the case following the embodiment has denser gold nanoparticle coating than the case following the comparative example.

Figure 5A:
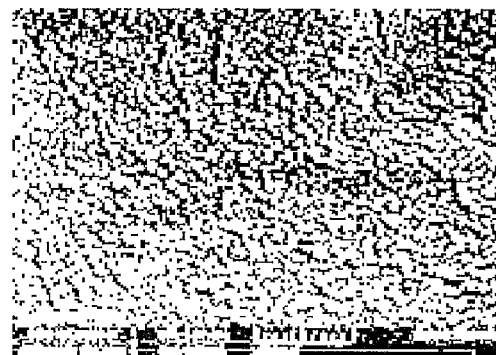
FIGS. 5a and 5b are scanning electron microscopy (SEM) images of gold nanoparticle arrays manufactured referring to the embodiment and the comparative example, respectively, in the present invention.
Figure 5B:
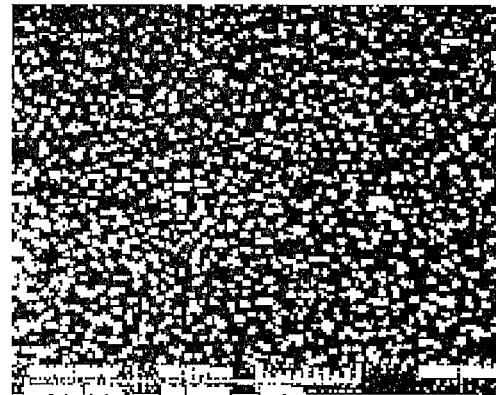

FIGS. 5a and 5b are scanning electron microscopy (SEM) images of the gold nanoparticle arrays manufactured referring to the embodiment and comparative example, respectively. The substrate used is polycarbonate (PC).

Referring to FIGS. 5a and 5b, the case following the embodiment leads to more homogeneous and higher density coating of gold nanoparticles on the substrate, as compared with the case following the comparative example.

From those results, referring to the embodiment of the present invention, it is possible to achieve high density coating of gold nanoparticles on the substrate in a shorter time. The previously stated embodiment is for gold nanoparticles, but it can be applied to the previously stated other conductive nanoparticles because a specific binding of conductive nanoparticles to the binder is not necessarily required. Thus, the present invention is not limited to the above stated embodiment.

In the case of wet coating of conductive nanoparticles in an electric field (a constant or alternating electric field, preferably an alternating electric field), in the mixed solution of the conductive nanoparticles and the ionic binders, the conductive nanoparticles bound together with ionic binders can have kinetic energy by the electric field and then be activated. Like this, the activated ionic polymers or conductive nanoparticles can increase their flux delivered onto the surface of the substrate and provide a strong immobilization force on the surface of the polymer substrate. Accordingly, in an electric field induced-wet process, a coating speed of conductive nanoparticles increases and thus it is possible to obtain a high density coating of the nanoparticles on the substrate. In addition, referring to the embodiment of the present invention, the wet process allows a mass production as well as a low temperature process which enables to use a polymeric substrate having weak heat resistance and thus to manufacture light-weight cost-effective sensors. These merits will be clearer in the following.

Figure 6A:
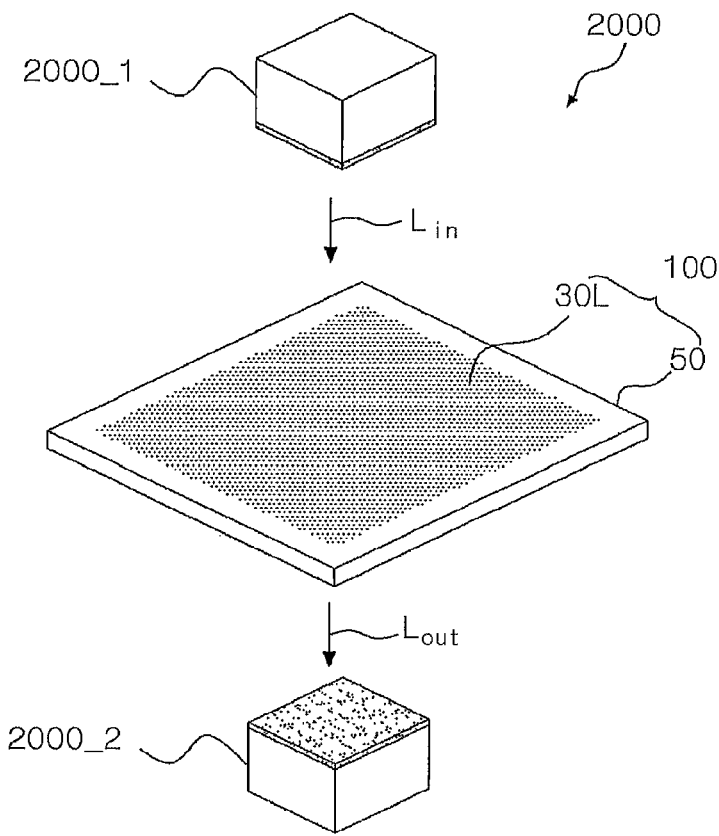
FIG. 6a is a schematic illustration of a spectrophotometer referring to the embodiment in the present invention and FIG. 6b illustrates a cuvette for a spectroscopic analysis referring to the first embodiment in the present invention.

Referring to the embodiment of the present invention, an SPR-based spectroscopic analysis sensor, like the one illustrated in FIG. 2d, was manufactured and its absorbance change was measured at the setup illustrated in FIG. 6a using a UV-VIS spectrophotometer (2000) sold under the trademark Thermo Scientific™ GENESYS™ having a basic setup illustrated in FIG. 6a. In addition, a spectroscopic analysis sensor (100) can be manufactured as a spectroscopic analysis cuvette (300A) like the one illustrated in FIG. 6b.

Referring to FIG. 6a, the spectrophotometer (2000) comprises a light emission part (2000_1), a transparent substrate (50), a SPR- or LSPR-based sensor comprising a conductive nanoparticle array (30L) formed on the main surface of the transparent substrate, and a light detection part (2000_2). The light emission part (2000_1) can emit light passing through the transparent substrate (50). Preferably, the light can be emitted to the direction perpendicular to the transparent substrate (50), but the present invention is not limited to that. In some embodiments, the light emission part (2000_1) and the light detection part (2000_2) can be placed opposite each other against the sensor (100). However, the present invention is not limited to this. Depending on the measurement mode of the transmitted light or reflected light, or the combination of appropriate optical devices such as reflectors or lenses, the present invention can have a setup in which the light emission part (2000_1) and the light detection part (2000_2) are not oppositely placed. The above stated light can have a wavelength between 380 nm and 1,500 nm, covering the ultraviolet and visible regions of the electromagnetic wave.

One, two or more sensors (100) can be placed along the light path between the light emission part (2000_1) and the light detection part (2000_2). The setup having more than 2 sensors will be described later referring to FIG. 8. The spectrophotometer (2000) analyzes by measuring change of absorbance or an absorption wavelength showing a maximum signal, calculated from the light emitted from the light emission part (2000_1) and the light arrived to the light detection part (2000_2).

The above stated degree of change in the absorbance and the absorption wavelength is based on the LSPR phenomenon and derived from change of an effective refractive index around the conductive nanoparticles depending on the reactivity of biological or non-biological substances, in samples, contacting with the above stated conductive nanoparticles. As stated previously, change of the absorbance and the absorption wavelength and thus a sensitivity can be improved through the high density coating of conductive nanoparticles. The spectrophotometer (2000) can contain an additional analysis module (not illustrated) for analyzing the above stated target analytes. The above stated analysis module can comprise, but not limited to, a computing system such as a typical microprocessor, memory and storage device.

Figure 6B:
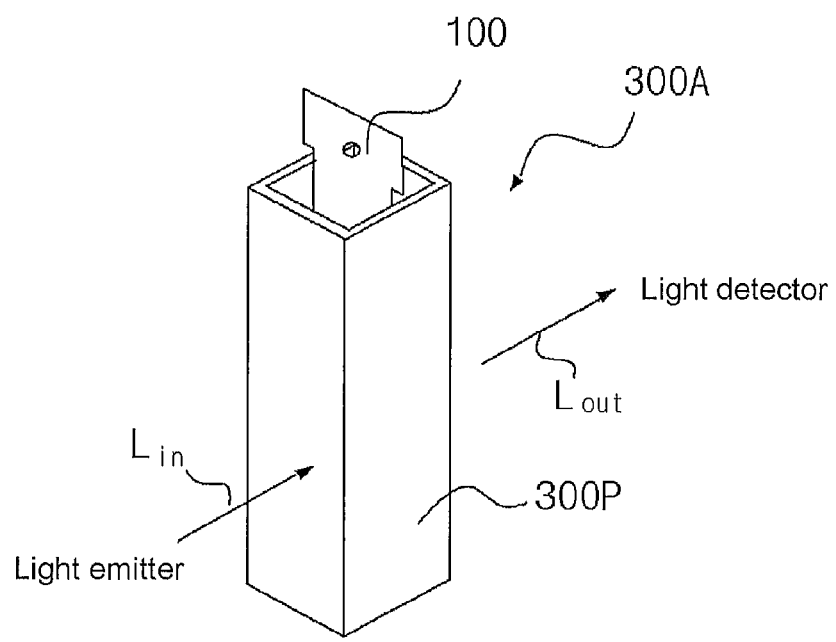

Referring to FIG. 6b, because the cuvette (300A) is made with a transparent material, the light (Lin) emitted from the light emission part can pass through the sensor (100) and the passed light (Lout) can be delivered to the light detection part. Even not illustrated here, the cuvette (40) can contain an additional holding part inside for holding the sensor (100) and an additional injection part for injecting reaction samples containing target analytes.

Figure 7:
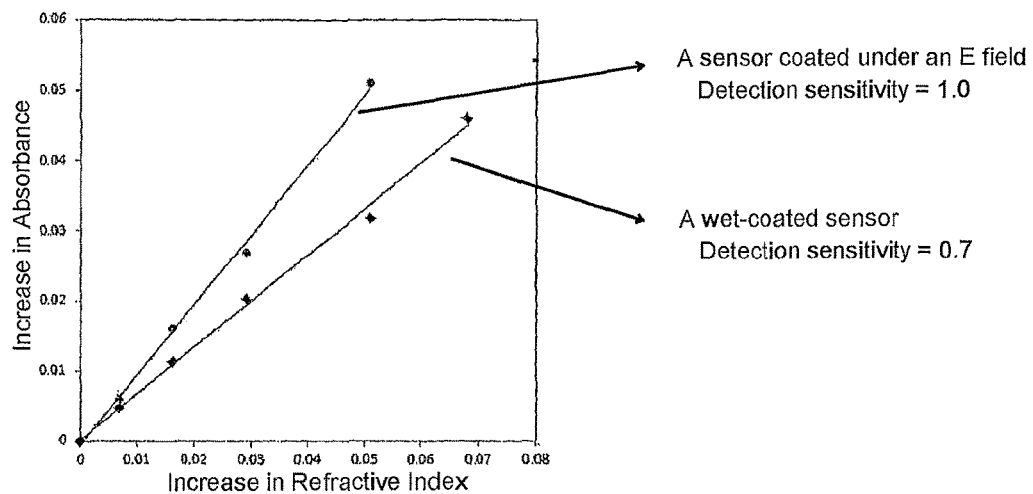
FIG. 7 shows graphs illustrating response levels of the sensors, measured using a spectrophotometer, referring to the embodiment and the comparative example, respectively, in the present invention.

FIG. 7 shows graphs of the sensor sensitivities measured by using the spectrophotometer (FIG. 6a_2000) referring to the embodiment and comparative example, respectively.

Referring to FIG. 7, the degree of an absorbance value change against a refractive index value change of the sensor is enhanced more than 43% when following the embodiment, as compared when following the comparative example. The enhancement confirms the measurement sensitivity enhanced that much due to the high density of the conductive nanoparticles coated.

Figure 8:
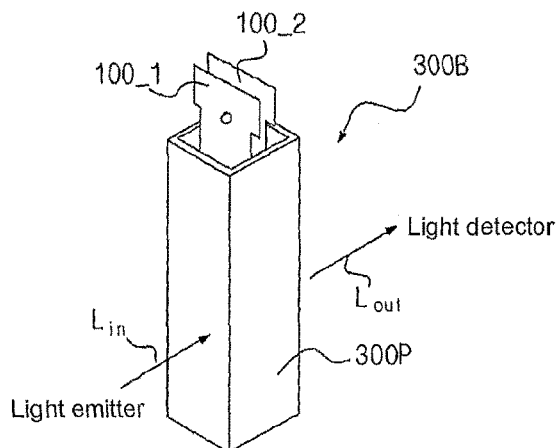
FIG. 8 is a perspective view of a cuvette referring to another embodiment in the present invention.

FIG. 8 is a perspective view of the cuvette (300B) referring to the embodiment of the present invention.

Referring to FIG. 8, the cuvette (300B) contains two SPR- and LSPR-based sub-sensors (100_1, 100_2) placed along the beam path between the light emission part and the light detection part of the spectrophotometer (FIG. 6a_2000). In this case, each conductive nanoparticle array (30L) on the sub-sensors (100_1, 100_2) can have same or different coating density or coating thickness. In the case of using multiple number of sensors comprising conductive nanoparticle arrays with different optical properties, it is possible to have simultaneous acquisition of absorbance at wavelengths showing different optical properties so as to analyze 2 or more substances at a time.

In another embodiment, each of the sensors (100_1, 100_2) can include immobilization substances which can bind with same or different target analytes and thus the sensors can be used for simultaneous spectroscopic analysis of multiple number of same or different samples.

Referring to the previously stated embodiments, use of multiple number of sensors spatially stacked along the beam path between the light emission part and light detection part, in a SPR- or LSPR-based analysis, can amplify measurement sensitivity practically as much as number of the sensor used, through an effect of practical enhancement of conductive nanoparticle density per unit transmitted area.

Figure 9A:
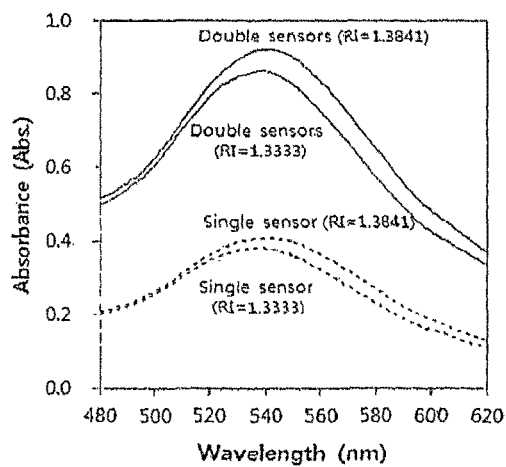
FIGS. 9a and 9b are graphs showing wavelength-dependent absorbance and amount of absorbance change, respectively, in the absorption spectra measured using 1-3 LSBR-based sensors for the samples having different refractive indexes, referring to the first embodiment in the present invention.
Figure 9B:
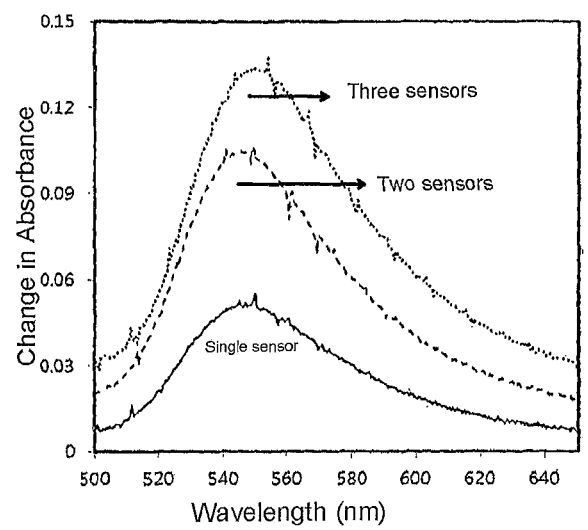

FIGS. 9a and 9b are graphs showing wavelength-dependent absorbance and absorbance change, respectively, in the absorption spectra measured using 1-3 LSPR-based sensors for the samples having refractive indexes different each other, referring to the first embodiment of the present invention.

Referring to FIG. 9a, the refractive index(RI) of distilled water at room temperature is 1.3333, the refractive index of 40% glycerol at room temperature is 1.3841, and those refractive indexes are same for LSPR-based sensors composed of 1, 2 or 3 units. However, the amount of absorbance increase and thus the amount of LSPR detection signal increase, at wavelengths within a specific range, increases about twice upon measuring using 2 sensors and about triple times upon using 3 sensors, as compared with measuring using a unit sensor.

Therefore, it is clear that absorbance increases twice or more upon spatial stacking of multiple number of the sensors followed by placing them along the beam path. As a result, referring to the embodiment of the present invention, it is possible to increase detection sensitivity easily in a SPR-based spectroscopic analysis by using multiple number of sensors.

The table 1 below shows detection sensitivities (the comparative examples 1 and 2) taken from the published corresponding articles about SPR-based spectroscopic analysis experiments using conductive nanoparticles and detection sensitivities (the embodiments 1 to 3) measured upon increasing number of analysis sensors referring to the embodiments of the present invention.

TABLE 1

| Example of experiment | Sensor | Detection limit (absorbance change/ refractive index change) |
|---|---|---|
| Embodiment 1 | 1 sensor | 1.0 |
| Embodiment 2 | 2 sensors | 2.0 |
| Embodiment 3 | 3 sensors | 2.6 |
| Comparative example 1 (Anal Chem 2004, 76, 5370-5378) | Nanostructures on glass substrates | 1.2 |
| Comparative example 2 (Microelectronic Engineering 86 (2009) 2437-2441) | Nanostructures on glass substrates | 0.7 |
| Comparative example 3 (Anal Chem 2002, 74, 504-509) | Nanostructures on glass substrates | 0.5 |

Referring to the table 1, a detection sensitivity and thus an intensity of a LSPR signal is measured differently depending on kind of spectrophotometers and number of sensors. Especially, referring to the embodiment of the present invention, it is clear that an intensity of a LSPR signal (a ratio of absorbance change to unit refractive index change) increases almost linearly as number of the sensor increases. It is also clear that in the case of using 2 or more sensors, the slope of reaction is greater than that obtained when analyzing referring to the comparative examples 1 and 2. Thus, referring to the embodiment of the present invention, it is possible to detect target analytes more sensitively and accurately because the slope of reaction increases in the same medium.

Referring to FIG. 9b, similar to the graph in FIG. 9a, in the case of using mediums having the same refractive index, it is clear that in various wavelength ranges, using 2 sensors increases the degree of absorbance change in optical absorption spectra about twice and using 3 sensors increases the degree of absorbance change more than three times, as compared with using a unit sensor.

Figure 10:
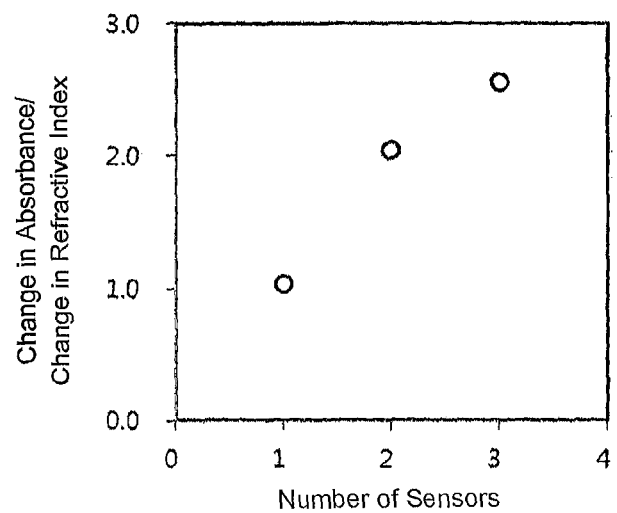
FIG. 10 is a graph showing a relationship between an absorbance change and a refractive index change measured using 1-3 LSPR sensors.

FIG. 10 is a graph showing a relationship between refractive index change and absorbance change, measured using one or two LSPR sensors.

Referring to FIG. 10, it is clear that the ratio of the absorbance change to refractive index change is about 1.0 when using a unit sensor, but the ratio is about 2.0 when using 2 LSPR sensors and increases to about 2.6 when using 3 LSPR sensors.

In the previously stated various embodiments, the spectrophotometer can be modified as below and that is also included within the scope of the present invention. For an example, to use a well-plate reader and a microplate reader together with the above stated sensors, unlike the illustration in FIG. 6a, the light emission part and the light detection part can be aligned to upper and lower parts, respectively, with respect to the well-plate reader placed flat. In this case, the above stated sensors should be manufactured to sizes small enough to be put in each well of the well-plate and the sensors can be aligned as an array form so as to put them simultaneously into the well.

In addition, each substrate of the sensors can be arrayed in a parallel direction to the light emission part and the light detection part which are placed upper and lower parts, respectively. To apply 2 or more sensors to unit well, each sensor, for example, can be spatially separated and stacked as a pair of two sensor sheets in a perpendicular direction. In another embodiment, multiple number of LSPR sensors can be attached to a microfluidic device opposite each other and be repeatedly stacked with spacers between them to provide various flow channels. In another embodiment, the above LSPR sensor can be selectively used to the topmost layer and/or the bottom layer of the array for amplifying LSPR-based absorbance several times.

Referring to the embodiment of the present invention, the manufacturing cost can be reduced because a low temperature wet process is possible and thus a substrate of a polymer material allowing easy molding and processing can be used. In addition, according to the embodiment of the present invention, a quick analysis of various substances is possible because a target analyte analysis is possible using a LSPR phenomenon without any pretreatment step for attaching marker substances like fluorophores.

It is very clear that the present invention stated up to now is not limited to the previously stated embodiments and drawings and thus various substitutions, modifications and alterations are possible within the scope not deviated from the technical idea of the present invention, to people having general knowledge in the technical fields to which the present invention belongs.

What is claimed is:

1. A method of fabricating a substrate of a sensor, the method comprising:
providing a solution comprising an ionic binder and conductive nanoparticles;
dipping the substrate into the solution; and
generating a plasma discharge over the solution having the substrate dipped therein using electrodes that are outside of the solution, thereby causing the conductive nanoparticles to be coated on the substrate.

2. The method of claim 1, wherein the solution is in the form of a gel comprising the ionic binder and the conductive nanoparticles.

3. The method of claim 1, wherein the ionic binder comprises one or more selected from the group consisting of poly diallyldimethylammonium chloride, poly allylamine hydrochloride, poly 4-vinylbenzyltrimethyl ammonium chloride, polyethyleneimine, poly acrylic acid, poly sodium 4-styrene sulfonate, poly vinylsulfonic acid, a poly sodium salt and a poly amino acid.

4. The method of claim 1, wherein the substrate comprises a transparent material.

5. The method of claim 1, wherein the substrate comprises a polymer substrate.

6. The method of claim 1, wherein generating the plasma discharge comprises applying an electric field using the electrodes to a gas mixture comprising one or more gas(es) selected from the group consisting of helium, neon, argon, nitrogen and air.

7. The method of claim 1, wherein the conductive nanoparticles have one or more shapes selected from the group consisting of a sphere, a tube, a column, a rod, a hollow, a pore and a wire.

8. The method of claim 1,
wherein the conductive nanoparticles are formed of one or more conductive materials selected from the group consisting of carbon, graphite, a metalloid, a metal, a conductive metal oxide, and a conductive metal nitride or
wherein the conductive nanoparticles comprise a dielectric core and a conductive shell, the conductive shell being formed of one or more conductive materials selected from the group consisting of carbon, graphite, a metalloid, a metal, a conductive metal oxide and a conductive metal nitride.

9. The method of claim 8,
wherein when the one of more conductive materials of the nanoparticles or the conductive shell includes a metalloid, the metalloid is a first element or a first alloy having an element selected from the group consisting of antimony, germanium and arsenic,
wherein when the one of more conductive materials of the nanoparticles or the conductive shell includes a metal, the metal is a second element or a second alloy having an element selected from the group consisting of titanium, zinc, aluminum, scandium, chromium, manganese, iron, cobalt, nickel, copper, indium, tin, yttrium, zirconium, niobium, molybdenum, ruthenium, rhodium, palladium, gold, silver, platinum, strontium, tungsten, cadmium and tantalum,
wherein when the one or more conductive materials of the nanoparticles or the conductive shell includes a conductive metal oxide, wherein the conductive metal oxide is formed of one or more materials selected from the group consisting of indium tin oxide, indium zinc oxide, aluminum-doped zinc oxide, gallium indium zinc oxide and zinc oxide; and
wherein when the one of more conductive materials of the nanoparticles or the conductive shell includes a conductive metal nitride, the metal nitride is formed of tungsten nitride.

10. The method of claim 1, wherein causing the conductive nanoparticles to be coated on the substrate comprises causing the conductive nanoparticles to be arranged to propagate a surface plasmon polariton (SPP) at a wavelength corresponding to a localized surface plasmon resonance condition.

11. The method of claim 1, further comprising attaching an immobilization molecule to at least some of the conductive nanoparticles, wherein the immobilization molecule is configured to specifically bind to one or more target analytes.

12. The method of claim 11, wherein the immobilization molecule comprises a molecule selected from the group consisting of antigens, antibodies, proteins, peptides, DNA, RNA, PNA, enzymes, enzyme substrates, hormones, hormone receptors, and a synthetic chemical having a functional group, wherein the functional group is configured to bind to the one or more target analytes.

13. The method of claim 1, wherein the substrate is an insulating material.

14. The method of claim 1, wherein the substrate comprises a material selected from the group consisting of sapphire, glass, single crystal silicon, silicone rubber, latex, a metal plate, a magnetic material, a silicon oxide, and a polymer material.

15. The method of claim 14, wherein substrate comprises the polymer material, wherein the polymer material is selected from the group consisting of polycarbonate, polyethylene terephthalate, polymethyl methacrylate, triacetyl cellulose, cyclic olefin, polyarylate, polyacrylate, polyethylene naphthelate, polybutylene terephthalate and polymide.

16. The method of claim 1, wherein method comprises fabricating a plurality of substrates, the method comprising:
dipping a second substrate into the solution simultaneously with the substrate,
wherein the second substrate has a main surface that is separated and in parallel to a main surface of the substrate; and
wherein generating the plasma discharge causes the conductive nanoparticles to be simultaneously coated on the main surface of the substrate and the main surface of the second substrate.

17. The method of claim 1, wherein dipping the substrate into the solution comprises submerging the substrate in the solution while generating the plasma discharge.

18. The method of claim 5, wherein the conductive nanoparticles are caused to coat a polymeric surface of the polymer substrate.

19. The method of claim 1, wherein generating the plasma discharge is conducted at atmospheric pressure.

20. The method of claim 1, wherein the substrate comprises an opaque material.

21. The method of claim 1, wherein the solution further comprises one or more solvent(s) selected from the group consisting of distilled water, deionized water, aliphatic alcohols, aliphatic ketones, eaters of aliphatic carboxylic acids, imides of aliphatic carboxylic acids, aromatic hydrocarbons, aliphatic hydrocarbons, acetonitrile and aliphatic sulfoxides.

22. The method of claim 21, wherein the solution comprises, on the basis of a total weight of the solution, the ionic binder at 0.01 wt. %-0.3 wt. %, the conductive nanoparticles at 0.1 wt. %-0.3 wt. % and a balance comprising the solvent.

* * * * *

UNITED STATES PATENT AND TRADEMARK OFFICE
CERTIFICATE OF CORRECTION

PATENT NO. : 10,359,362 B2
APPLICATION NO. : 14/784569
DATED : July 23, 2019
INVENTOR(S) : Gibum Kim Page 1 of 1

It is certified that error appears in the above-identified patent and that said Letters Patent is hereby corrected as shown below:

On the Title Page

Page 3 Column 1, Line 8 (Item (56)), under Other Publications, change "KCI" to --KCl--.

Page 3 Column 2, Line 25 (Item (56)), under Other Publications, change "Biolnterface" to --BioInterface--.

In the Specification

Column 4, Line 60, change "polyethyleneimine an" to --polyethyleneimine. An--.

Column 5, Line 66, change "methacylate)" to --methacrylate)--.

Column 6, Line 1, change "naphthelate," to --naphthalate,--.

In the Claims

Column 14, Line 13 (approx.), in Claim 15, change "naphthelate," to --naphthalate,--.

Column 14, Line 13 (approx.), in Claim 15, change "polymide." to --polyimide.--.

Signed and Sealed this
Seventeenth Day of November, 2020

Andrei Iancu
*Director of the United States Patent and Trademark Office*